United States Patent [19]

Diercks et al.

[11] Patent Number: 5,401,884
[45] Date of Patent: Mar. 28, 1995

[54] PREPARATION OF FORMALDEHYDE BY OXIDATIVE DEHYDROGENATION OF METHANOL IN THE PRESENCE OF DINITROGEN OXIDE

[75] Inventors: Rainer Diercks, Neuhofen; Manfred Essig, Otterberg; Laszlo Marosi, Ludwigshafen, all of Germany

[73] Assignee: BASF Aktiengesellschaft, Ludwigshafen, Germany

[21] Appl. No.: 239,321

[22] Filed: May 6, 1994

[30] Foreign Application Priority Data

May 12, 1993 [DE] Germany .................. 43 15 799.8

[51] Int. Cl.$^6$ ................ C07C 47/52; C07C 45/29
[52] U.S. Cl. ........................................ 568/487
[58] Field of Search ............................. 568/487

[56] References Cited

U.S. PATENT DOCUMENTS

| 2,667,513 | 1/1954 | McKinnis | 568/487 |
| 4,072,717 | 2/1978 | Halbritter et al. | 568/487 |
| 4,119,673 | 10/1978 | Aicher et al. | 568/487 |
| 4,209,466 | 6/1980 | Wolf et al. | 568/487 |
| 4,233,248 | 11/1980 | Rao et al. | 568/487 |

FOREIGN PATENT DOCUMENTS 2442231 3/1976 Germany .
2121787 4/1984 United Kingdom .

*Primary Examiner*—Werren B. Lone
*Attorney, Agent, or Firm*—Keil & Weinkauf

[57] ABSTRACT

Formaldehyde is prepared by oxidative dehydrogenation of methanol in the gas phase on a silver or silver-containing catalyst by means of an oxygen-containing gas which contains dinitrogen oxide.

1 Claim, No Drawings

PREPARATION OF FORMALDEHYDE BY OXIDATIVE DEHYDROGENATION OF METHANOL IN THE PRESENCE OF DINITROGEN OXIDE

The present invention relates to a process for the preparation of formaldehyde by oxidative dehydrogenation of methanol by means of an oxygen-containing gas in the gas phase on a silver or silver-containing catalyst.

It is generally known that formaldehyde can be prepared by oxidative dehydrogenation of methanol in the presence of silver catalysts at elevated temperature (Ullmanns Encyklopädie der Technischen Chemie, 4th Edition, Volume 11, pp. 611 ff.), where essentially the following reactions take place on the silver catalyst:

$$CH_3OH + \tfrac{1}{2}O_2 \rightarrow CH_2O + H_2O$$

$$CH_3OH \rightleftharpoons CH_2O + H_2$$

$$H_2 + \tfrac{1}{2}O_2 \rightarrow H_2O$$

In known processes, there is still room for improvement with respect to the yield. There have been various attempts to improve the yield.

Thus, GB-A 2,121,787 describes the use of specific silver/palladium alloys, but simple electrolytic catalyst regeneration causes problems in this procedure.

DE-A 24 42 231 converts methanol in a mixture with steam and air into formaldehyde on a silver catalyst, it being intended for part of the reaction offgas to be recycled.

U.S. Pat. No. 4,223,248 discloses a process for the preparation of formaldehyde from methanol on a silver-containing catalyst, where the oxidizing gas employed is exclusively dinitrogen oxide.

However, these processes have the disadvantage that they still cannot be regarded as satisfactory with respect to the yields or do not allow further improvements with respect to the offgas quality and residual methanol contents or only do so by means of complex equipment.

It is an object of the present invention to provide an improved process which facilitates an increase in selectivity and yield in a simple manner and does not affect catalyst work-up.

We have found that this object is achieved by a process for the preparation of formaldehyde by oxidative dehydrogenation of methanol in the gas phase on a silver or silver-containing catalyst by means of an oxygen-containing gas which contains from 1 to 50% by volume of dinitrogen oxide.

Suitable starting materials for the process are pure methanol, technical-grade methanol, crude methanol or advantageously mixtures thereof with water; the methanol concentration in the aqueous mixtures is expediently from 40 to 95% by weight, preferably from 50 to 85% by weight. The methanol is fed to the reactor space in vapor form, advantageously as a mixture with steam and, if desired, an inert gas, for example nitrogen.

The oxidant used is an oxygen-containing gas. According to the invention, a mixture of from 99 to 50% by volume of air and from 1 to 50% by volume, preferably from 2 to 30% by volume, particularly preferably from 7 to 25% by volume, of dinitrogen oxide ($N_2O$) is used. The amount of $N_2O$ should be selected so that the molar ratio between methanol and $N_2O$ is in the range from 55:1 to 3.5:1, preferably from 15:1 to 4.0:1, particularly preferably from 7:1 to 4.5:1.

$N_2O$ is available as an undesired byproduct from a number of industrial-scale processes, for example from the synthesis of adipic acid or hydroxylamine, where it must be disposed of. The present invention allows the specific use of $N_2O$ in an industrial-scale process.

For technical reasons, it is advisable for the $N_2O$ to be fed to the starting material mixture in the form of a mixture with nitrogen.

The starting materials are fed in a manner known per se through a silver-containing fixed-bed catalyst installed in a vertical tubular reactor. The catalyst preferably comprises silver crystals having a particle size of from 0.1 to 3 mm, in particular from 0.2 to 2.5 mm. The fixed-bed catalyst can have a multilayer structure through arrangement of the silver crystals in layers of different particle size. The catalyst bed preferably has a multilayer structure, as described in DE-B 23 22 757.

The starting mixture of methanol vapor, oxygen-containing gas, $N_2O$ and, if used, steam and inert gas is preferably passed through the tubular reactor from top to bottom.

Otherwise, the process is carried out in one step in a manner known per se by passing the starting mixture through the fixed catalyst bed at from 550° to 750° C., in particular from 600° to 720° C., particularly advantageously at from 660° to 700° C. The process is preferably carried out continuously at from 0.5 to 3 bar, in particular at from 0.8 to 2 bar, preferably at from 1 to 1.5 bar. The residence times in the catalyst zone are from 0.001 to 1 second, preferably from 0.002 to 0.1 second. The reaction gases leaving the catalyst zone are advantageously cooled within a short time, for example to below 350° C. The cooled gas mixture can expediently be fed to an adsorption tower, in which the formaldehyde is washed out of the gas mixture by means of water.

The process according to the invention for the preparation of formaldehyde gives advantageous yields, high conversional and high selectivity in a simple manner. Furthermore, the process according to the invention suppresses oxidation of the hydrogen formed during the thermal dehydrogenation to water, which results in higher hydrogen contents in the offgas and thus in better energy yields on combustion or larger amounts of hydrogen on $H_2$ removal.

It is also advantageous that the residual methanol contents can be reduced, making distillative methanol enrichment superfluous for a number of applications. In addition, $N_2O$, which is present as an undesired byproduct, can be utilized, offering a further economic advantage.

The following experiments were carried out in an existing plant, with nitrogen being fed in order to keep constant the amount of offgas for which the plant was designed.

EXAMPLES 1 TO 4

The examples were carried out using a vertical reactor having an internal diameter of 2 cm and containing in its upper part a three-layer fixed catalyst bed with a total depth of 10 mm.

The lower layer comprised 4 g of silver having a particle size of from 0.75 to 1.0 mm, the middle layer comprised 7 g of silver having a particle size of from 0.4 to 0.75 mm, and the upper layer comprised 3 g of silver having a particle size of from 0.2 to 0.4 nun.

A mixture of 300 g of methanol and 200 g of water in vapor form axed the amounts of air or air/N₂O shown in the table was passed hourly through the catalyst bed from top to bottom. The reaction took place at 660° C./1.1 bar in the catalyst zone. After the reaction, the reaction mixture was cooled to 150° C. and taken up in water.

| Example No. | 1 | 2 | 3 | 4 |
|---|---|---|---|---|
| Air [l/h] | 380 | 335 | 290 | 245 |
| N₂O [l/h] | — | 15 | 30 | 45 |
| Conversion [%] | 97.9 | 98.5 | 98.9 | 99.1 |
| Selectivity [%] | 92.2 | 92.9 | 93.4 | 94.1 |

-continued

| Example No. | 1 | 2 | 3 | 4 |
|---|---|---|---|---|
| Yield [%] | 90.2 | 91.5 | 92.4 | 93.3 |
| H₂ content in the offgas[1] [% by vol.] | 18.0 | 20.2 | 21.8 | 24.3 |
| Residual methanol content[2] [%] | 2.3 | 1.5 | 1.3 | 1.1 |

[1] Offgas volume kept constant at 390 l by addition of N₂
[2] based on formaldehyde

We claim:
1. A process for the preparation of formaldehyde by oxidative dehydrogenation of methanol in the gas phase on a silver or silver-containing catalyst by means of an oxygen-containing gas which contains from 1 to 50% by volume of dinitrogen oxide.

* * * * *